(12) United States Patent
McCoy

(10) Patent No.: US 9,693,935 B2
(45) Date of Patent: Jul. 4, 2017

(54) PERSONAL CARE SOLID GRANULES THAT SUSTAIN ESSENTIAL OILS AND OR PLANT HERBAL EXTRACTS THAT EMULSIFY IN HOT WATER CREATING THERAPEUTIC SOLUTION

(71) Applicant: Sarah McCoy, Seattle, WA (US)

(72) Inventor: Sarah McCoy, Seattle, WA (US)

( * ) Notice: Subject to any disclaimer, the term of this patent is extended or adjusted under 35 U.S.C. 154(b) by 207 days.

(21) Appl. No.: 13/740,235

(22) Filed: Jan. 13, 2013

(65) Prior Publication Data

US 2014/0199351 A1    Jul. 17, 2014

(51) Int. Cl.
| | |
|---|---|
| *A61K 8/02* | (2006.01) |
| *A61Q 5/00* | (2006.01) |
| *A61Q 19/00* | (2006.01) |
| *A61Q 5/12* | (2006.01) |
| *A61Q 17/04* | (2006.01) |
| *A61K 8/34* | (2006.01) |
| *A61K 8/41* | (2006.01) |
| *A61K 8/46* | (2006.01) |
| *A61Q 5/02* | (2006.01) |
| *A61K 8/73* | (2006.01) |
| *A61Q 19/04* | (2006.01) |
| *A61Q 19/10* | (2006.01) |

(52) U.S. Cl.
CPC ............ *A61K 8/0216* (2013.01); *A61K 8/342* (2013.01); *A61K 8/416* (2013.01); *A61K 8/463* (2013.01); *A61K 8/737* (2013.01); *A61Q 5/02* (2013.01); *A61Q 5/12* (2013.01); *A61Q 19/00* (2013.01); *A61Q 19/04* (2013.01); *A61Q 19/10* (2013.01); *A61K 2800/48* (2013.01); *A61K 2800/596* (2013.01); *A61K 2800/72* (2013.01); *A61K 2800/80* (2013.01)

(58) Field of Classification Search
None
See application file for complete search history.

(56) References Cited

U.S. PATENT DOCUMENTS

| | | | | |
|---|---|---|---|---|
| 2005/0282895 | A1* | 12/2005 | Dosch et al. | 514/557 |
| 2006/0188460 | A1* | 8/2006 | Ambrosen et al. | 424/70.1 |
| 2006/0269502 | A1* | 11/2006 | Johnson et al. | 424/70.13 |
| 2007/0275021 | A1* | 11/2007 | Lee et al. | 424/401 |
| 2010/0173007 | A1* | 7/2010 | DiLeva | 424/537 |
| 2014/0017184 | A1* | 1/2014 | Fumagalli | C08F 220/06 424/59 |

\* cited by examiner

*Primary Examiner* — Robert A Wax
*Assistant Examiner* — Randeep Singh

(57) ABSTRACT

A Personal care 100% plant derived, biodegradable solid granules that sustain beneficial essential oils, and or plant/herbal extracts and emulsify in hot water to create an emulsified therapeutic solution is disclosed. This invention improves over existing liquids in that it's solid granule form is completely plant derived and biodegradable and can sustain essential oils and antioxidants without the requirement of chemical preservatives, and can be packaged in eco-friendly, compostable paper. It improves over existing solid forms in that it is a 100% water soluble granule that emulsifies easily in hot water to form an easy to use liquid product.

4 Claims, 4 Drawing Sheets

PERSONAL CARE SOLID GRANULES THAT SUSTAIN ESSENTIAL OILS AND OR PLANT HERBAL EXTRACTS THAT EMULSIFY IN HOT WATER CREATING THERAPEUTIC SOLUTION

REFERENCE TO RELATED APPLICATIONS

This patent application claims the benefit of U.S. Provisional Application No. 61/586,222 filed on Jan. 13, 2012, the disclosure of which is incorporated herein by reference in its entirety.

BACKGROUND OF THE INVENTION

Field of the Invention

The present invention relates to personal care product compositions, and more particularly to personal care product compositions in a granular solid form that do not require the addition of chemical preservatives, contains and sustains the therapeutic benefits of its components, utilizes greener packaging while retaining the familiar liquid form after reconstitution.

Description of Related Art

Current liquid personal care products require the addition of chemical preservatives. These chemical preservatives can be potentially irritating and are being shown to cause potential harm to the body.

The plastic bottles they come in pollute the environment. A solid form is more convenient to carry when traveling. However, the existing solid personal care products are not easy to use. Therefore, there is a desire for greener, cleaner personal care products and such products still retain the convenience and characteristics of a familiar liquid form personal care product.

The present invention improves over existing liquids in that it's solid granule form can sustain therapeutic organic essential oils and antioxidants without the requirement of chemical preservatives. It improves on existing solid forms in that it uses 100% water soluble ingredients that emulsify easily in hot water to form an easy to use liquid product.

The claimed invention differs in its unique solid granule formula in that it contains and sustains the therapeutic benefit of organic essential oils and antioxidants. It can be packaged in PCR (Post Consumer Resin) compostable paper as a solid and create a user-friendly, eco-friendly solution.

SUMMARY OF THE INVENTION

One object of the present invention is to provide a process for preparing personal care products which can circumvent the requirement of adding chemical preservatives that can be potentially irritating and are being show to cause potential harm to the body.

Another object of the present invention is to provide a process for preparing personal care products which can make the product solid granular form to sustain therapeutic organic essential oils and antioxidants.

A further object of the present invention is to provide a process for preparing personal care products which improves over existing solid (solid form is more convenient to carry when traveling however existing solid forms are not easy to use) forms in that it creates a 100% water soluble granule composition that can emulsify easily in hot water to form an easy and familiar to use liquid product.

Still another object of the present invention is to provide a greener cleaner product. The present invention may be carried in PCR compostable paper as a solid and create a user-friendly, eco-friendly solution.

A method of preparing personal care product according to the present invention comprises the steps of heating/mixing plant derived, water soluble surfactants and other plant derived water-soluble emulsifiers/thickener in a container; heating the mixture until fully melted at about 45 degrees Celsius; removing the product from heat and adding essential oil, bacteria/mold protectors, vitamins/herbal extract; mixing the product until its uniform; and pouring the product into a mold to cool to a solid mass. Once the product is cooled, process the solid mass to form granules.

The products prepared this way can be packaged in PCR compostable paper and thus it provides a user-friendly, eco-friendly solution. Also, it is convenient to carry a solid form personal care product onto the airplane or when traveling on the road. Moreover, the 100% water soluble granules can be reconstituted, dissolved and emulsified easily in hot water to form an easy and familiar to use liquid product as conventional liquid form personal care products.

The more important features of the invention have thus been outlined in order that the more detailed description that follows may be better understood and in order that the present contribution to the art may better be appreciated. Additional features of the invention will be described hereinafter and will form the subject matter of the claims that follow.

Before explaining at least one embodiment of the invention in detail, it is to be understood that the invention is not limited in its application to the details of construction and the arrangements of the components set forth in the following description or illustrated in the drawings. The invention is capable of other embodiments and of being practiced and carried out in various ways. Also it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

The foregoing has outlined, rather broadly, the preferred feature of the present invention so that those skilled in the art may better understand the detailed description of the invention that follows. Additional features of the invention will be described hereinafter that form the subject of the claims of the invention. Those skilled in the art should appreciate that they can readily use the disclosed conception and specific embodiment as a basis for designing or modifying other structures for carrying out the same purposes of the present invention and that such other structures do not depart from the spirit and scope of the invention in its broadest form.

BRIEF DESCRIPTION OF THE DRAWINGS

Other aspects, features, and advantages of the present invention will become more fully apparent from the following detailed description, the appended claim, and the accompanying drawings in which similar elements are given similar reference numerals.

DESCRIPTION OF THE PREFERRED EMBODIMENT

Figure 1:
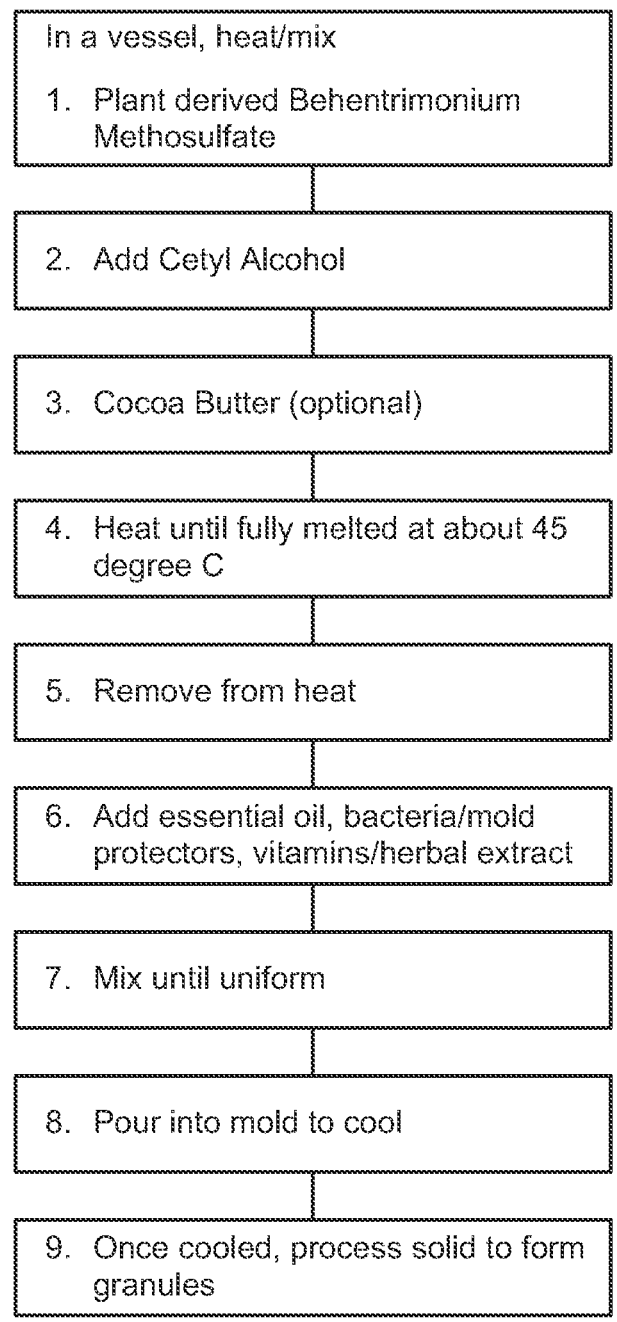
FIG. 1 is a flow chart showing how to make a conditioner according to one embodiment of the present invention.

Referring to FIG. 1, there is disclosed a flow chart on how to make a conditioner. In a container, heating/mixing plant derived behentrimonium methosulfate (or other plant derived, water soluble surfactant/s) 1; adding Cetyl Alcohol (or other plant derived water-soluble emulsifiers/thickener) to the container 2; adding Cocoa Butter (optional) to the container 3; heating the product mixture until fully melted at about 40-60 degrees Celsius, preferably 60 degrees Celsius 4; removing the product from heat 5 and adding at least one essential oil/or herbal extract, bacteria/mold inhibitor, vitamins 6; mixing the product until it is uniform 7; and pouring the product into a mold to cool 8. Once the product is cooled, take the solid mass out of the mold and process the solid mass into granules 9. The granules' size of the product range from 150 mesh to 5 mm.

Figure 2:
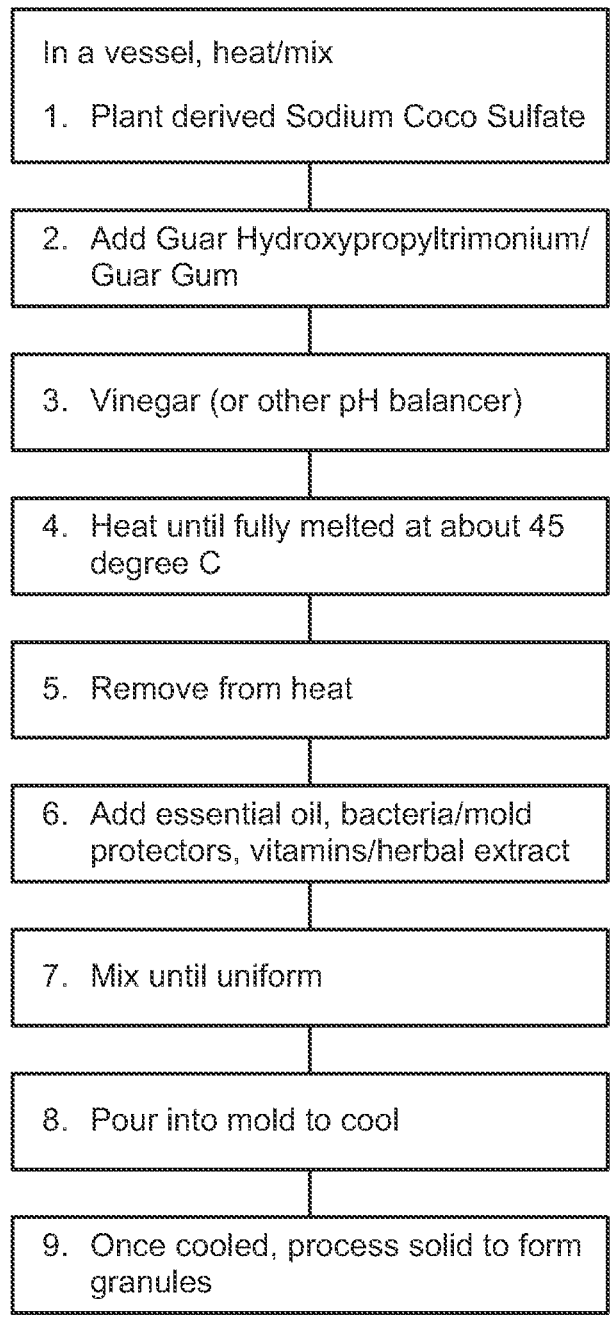
FIG. 2 is a flow chart showing how to make a shampoo according to one embodiment of the present invention.

Referring to FIG. 2, there is disclosed a flow chart on how to make a shampoo. In a container, heating/mixing plant derived Sodium Coco Sulfate (or other plant derived, water soluble surfactant/s) 1; adding vinegar (or other pH balancer) 2 to the container; heating until fully melted at about 40-60 degrees, preferably 60 degrees Celsius 3; removing the product from heat 4 and adding at least one essential oil/or herbal extract, bacteria/mold protectors, vitamins 5; mixing the product until it is uniform 6; guar gum is then added and blended until product is uniform and placing the product into a mold to cool 7. Once the product is cooled, take the solid mass out of the mold and process the solid mass into granules 9. The granules' size of the product range from 150 mesh to 5 mm.

Figure 3:
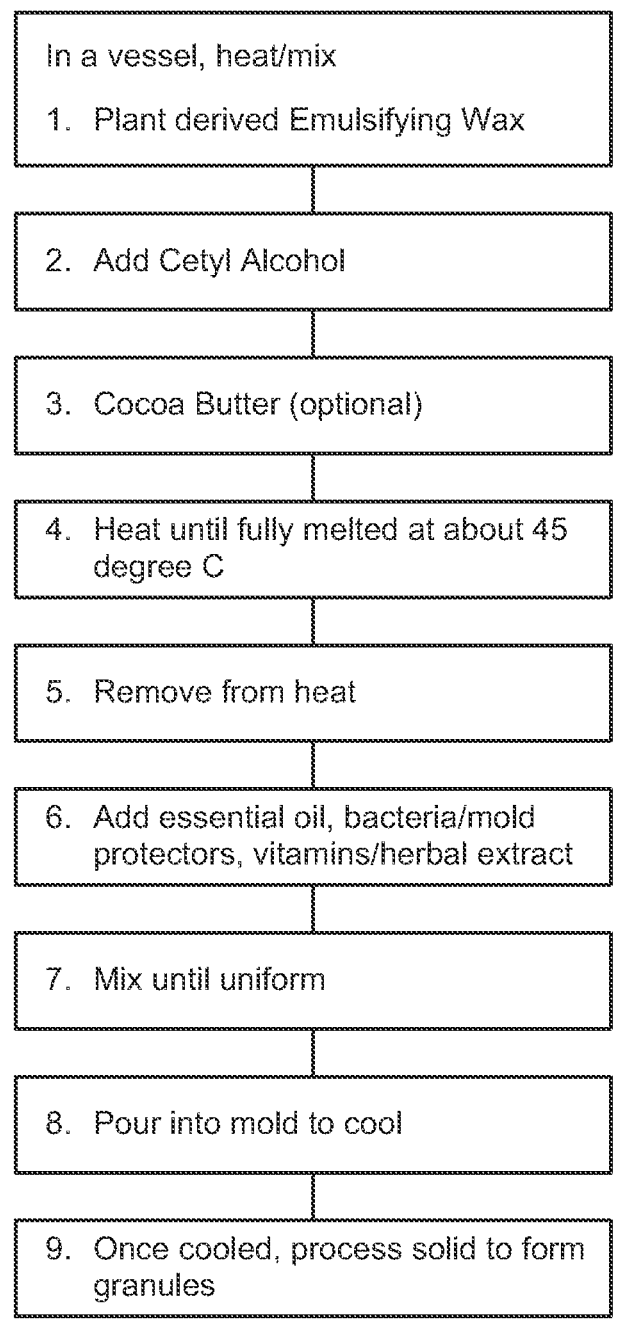
FIG. 3 is a flow chart showing how to make a lotion according to one embodiment of the present invention.

Referring to FIG. 3, there is disclosed a flow chart on how to make a lotion. In a container, heating/mixing plant derived Emulsifying Wax (or other plant derived, water soluble surfactant/s) 1; adding Cetyl Alcohol (or other plant derived water-soluble emulsifiers/thickener) to the container 2; adding Cocoa Butter (optional) to the container 3; or adding dihydroxyacetone (optional) 4; heating the mixture until fully melted at about 40-60 degrees, preferably 60 degrees Celsius 4; removing the product from heat 5 and adding at least one essential oil/or herbal extract, bacteria/mold protectors, vitamins 6; mixing the product until it is uniform 7; and pouring the product into a mold to cool 8. Once the product is cooled, take the solid mass out of the mold and process the solid mass into granules 9. The granules' size of the product range from 150 mesh to 5 mm.

The personal care product when comprising dihydroxyacetone in an amount of 8-20% is used for tanning lotion (FIG. 3)(said ingredient can also be included in a similar composition version of facial or body lotion).

The solidifying water soluble plant-derived surfactant is in an amount of 40-85%, preferably 12-60-80%, by weight of the product; the essential oil is in an amount of 2-10%, preferably 4%, by weight of the product; the vitamin is in an amount of 0.5-15%, preferably 8%, by weight of the product, the vitamin including panthenol.

More specifically, the solidifying water soluble plant-derived surfactant is selected from the group consisting of behentrimonium methosulfate, sodium coco sulfate, and emulsifying wax, and the solidifying water soluble plant-derived surfactant is in an amount of 40-85% by weight of the product.

The water soluble plant-derived emulsifier/thickener may be selected from the group consisting of cetyl alcohol and guar hydroxypropyltrimonium chloride in an amount of 2 2-20%, by weight of the product and preferably in an amount of 12% by weight of the product.

The pH balancer including vinegar or other pH balancer in an amount of 4-12% by weight of the product, wherein the pH balancer is blended with the water soluble surfactant and melted over the heat. The preferable amount of the pH balancer is 8% by weight of the product; the added amount is depending on the amount of other ingredients in the product.

The conditioning ingredient selected from the group consisting of cocoa butter and other conditioning ingredient in an amount of 2-20% by weight of the product, wherein the cocoa butter is blended with the water soluble surfactant and melted over the heat. The preferred amount of the cocoa butter is 16% by weight of the product.

The plant-derived antimicrobial ingredient in an amount of 1-4% by weight of the product, wherein the plant-derived antimicrobial ingredient including grapefruit seed extract or other antimicrobial ingredients.

The plant-derived ingredient that can inhibit growth of mold and yeast in an amount of 1-4% by weight of the product, wherein the plant-derived anti-mold and anti-yeast ingredient including potassium sorbate or other anti-mold and anti-yeast ingredients.

While the process outlined herein is in regard to shampoo related products such described process can also be employed with a facial or body wash formulation. Effectively, body wash, conditioners, facial lotion, as well as body lotion all lend themselves to this chemical composition formulation process.

Figure 4:
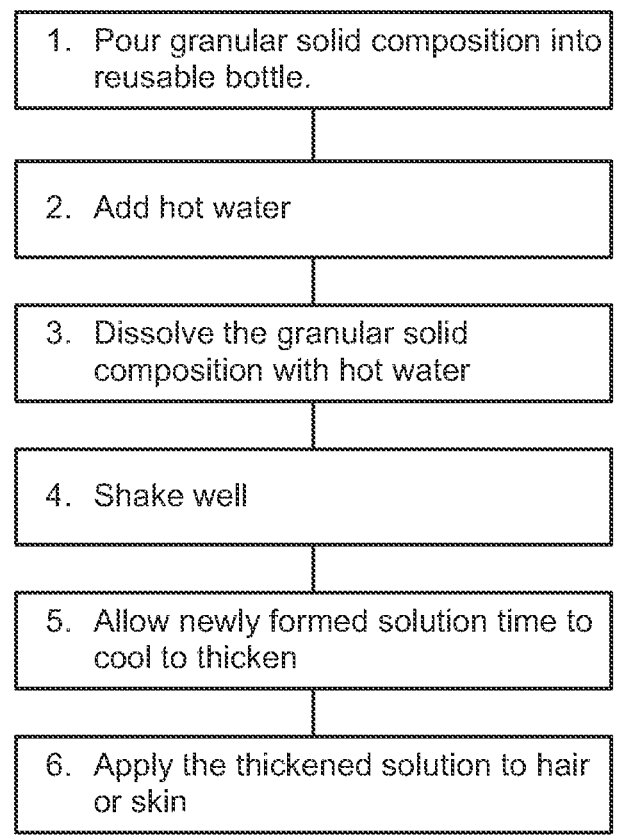
FIG. 4 is a flow chart showing how to use the personal care product according to the present invention.

Referring to FIG. 4, there is disclosed a method for applying an emulsified solution to hair/or skin of a person comprising: 1. pouring granular solid composition into reusable bottle; 2. adding hot water (a minimum temperature of 70-100 degrees Celsius, preferably about 80 degrees Celsius); 3. dissolving the granular solid composition with hot water at a minimum temperature of 70-100 degrees Celsius, preferably about 80 degrees Celsius, to form an emulsified solution (wherein the new formed liquid when cooled is what is applied externally to the hair/or skin); 4. shaking well; 5. allowing newly formed solution time to cool to thicken; and 6. applying the thickened solution to hair or skin as the composition is intended for.

Additionally, this invention could be sold in larger bulk packaging to be used for refilling glass containers/bottles, or smaller paper packets for travel.

While there have been shown and described and pointed out the fundamental novel features of the invention as applied to the preferred embodiments, it will be understood that the foregoing is considered as illustrative only of the principles of the invention and not intended to be exhaustive or to limit the invention to the precise forms disclosed. Obvious modifications or variations are possible in light of the above teachings. The embodiments discussed were chosen and described to provide the best illustration of the principles of the invention and its practical application to enable one of ordinary skill in the art to utilize the invention in various embodiments and with various modifications as are suited to the particular use contemplated All such modifications and variations are within the scope of the invention as determined by the appended claims when interpreted in accordance with the breadth to which they are entitled.

What is claimed is:

1. A hair care product having a water-soluble granular emulsified solid composition for topical use after reconstitution, the product comprising:
   a solidifying water soluble plant-derived surfactant selected from the group consisting of behentrimonium and salts thereof, and sodium coco sulfate; at least one additional solidifying water soluble plant-derived surfactant selected from the group consisting of an anionic surfactant, cationic surfactant, nonionic surfactant, amphoteric surfactant, and combinations thereof;
   at least one water soluble plant-derived emulsifier/thickener; at least one plant-derived antimicrobial ingredient; at least one plant-derived anti-mold/yeast ingredient; at least one essential oil/or herbal extracts;
   wherein the solidifying water soluble plant-derived surfactant is in an amount of 60.1-80% by weight of the product; the essential oils/or herbal extracts is in an amount of 2-10% by weight of the product; the antimicrobial ingredient is in an amount of 1-4% by weight of the product; and the anti-mold/yeast is in an amount of 1-4% by weight of the product, wherein said ingredients of the product are blended, and wherein the product is packaged for reconstitution for topical use.

2. The hair care product of claim 1, further comprising a pH balancer including citric acid in an amount of 4-12% by weight of the product, wherein the pH balancer is blended with the one or more water soluble plant-derived surfactants.

3. The hair care product of claim 2, further comprising at least one solid conditioning ingredient in an amount of 2-9% by weight of the product, wherein the solid conditioning ingredient is cocoa butter.

4. The hair care product of claim 3, wherein the water soluble plant-derived emulsifier/thickener is guar gum in an amount of 6-20% by weight of the product, and wherein the guar gum is blended with the one or more water soluble plant-derived surfactants.

* * * * *